US005693530A

United States Patent [19]

Schat et al.

[11] Patent Number: 5,693,530

[45] Date of Patent: Dec. 2, 1997

[54] MAREK'S DISEASE VIRUS NUCLEOTIDE SEQUENCE AND METHODS OF USE

[75] Inventors: Karel A. Schat, Ithaca, N.Y.; Kazuhiko Ohashi, Sapporo, Japan; Priscilla H. O'Connell, Ithaca, N.Y.

[73] Assignee: Cornell Research Foundation, Inc., Ithaca, N.Y.

[21] Appl. No.: 480,910

[22] Filed: Jun. 7, 1995

Related U.S. Application Data

[63] Continuation-in-part of Ser. No. 180,051, Jan. 11, 1994, abandoned.

[51] Int. Cl.$^{6}$ .......... C12N 15/86; C12N 15/38; A61K 39/255; A61K 39/295

[52] U.S. Cl. .......... 435/320.1; 424/199.1; 424/202.1; 424/229.1; 424/816; 536/23.1; 536/23.72; 930/224

[58] Field of Search .......... 424/229.1, 199.1, 424/202.1, 816; 435/172.1, 172.3, 320.1; 935/32, 23, 57, 65; 536/23.1, 23.72; 930/224

[56] References Cited

U.S. PATENT DOCUMENTS

| | | | |
|---|---|---|---|
| 4,160,024 | 7/1979 | Schat et al. | 424/229.1 |
| 4,980,162 | 12/1990 | Honda et al. | 424/202.1 |
| 5,171,677 | 12/1992 | Sakaguchi et al. | 435/172.3 |

FOREIGN PATENT DOCUMENTS

| | | |
|---|---|---|
| 0522535 | 1/1993 | European Pat. Off. . |
| 0334530 | 1/1995 | European Pat. Off. . |

OTHER PUBLICATIONS

Jones et al., "Marek Disease virus encodes a basic-leucine zipper gene resembling the fos/jun oncogenes that is highly expressed in lymphoblastoid tumors", Proc. Nat. Acad. Sci., 89:4042–4046, May 1992.

Kimmel, Meth. Enzymol., vol. 152: Guide to Molecular Techniques, Berger et al., eds. (New York: Harcourt Brace Johanovich, 1987), pp. 507–511.

Sakaguchi et al., "Marek's Disease Virus protein kinase gene identified within the short unique region of the viral genome is not essential for viral replication in cell culture and vaccine-induced immunity in chickens", Virol. 195: 140–148, 1993.

Yanagida et al., "Recombinant fowlpox viruses expressing the glysoprotein B homolog and the pp.38 gene of Marek's Disease virus", J. Virol. 66(3): 1402–1408, Mar. 1992.

Pratt et al., "Characterization of Reticuloendotheliosis Virus-Transformed Avian T-Lymphoblastoid Cell Lines Infected with Marek's Disease Virus", Journal of Virology, vol. 66, No. 12, 1992, pp. 7239–7244.

Ohashi et al., "cDNA Clones Derived From The Marek's Disease Tumor Cell Line MDCC-CU41" in Proceedings XIX World's Poultry Congress, 1992, pp. 54–57.

*Primary Examiner*—Mindy Fleisher
*Assistant Examiner*—Johnny F. Railey, II
*Attorney, Agent, or Firm*—Hodgson, Russ, Andrews, Woods & Goodyear

[57] ABSTRACT

A novel nucleotide sequence in the genome of Marek's disease virus (MDV) containing an open reading frame, whose expression is associated with lytic infection and tumor cell development in MDV-infected cells, is described. Also described is the use of this novel sequence for molecular diagnostics of serotype 1 MDV; and to generate a recombinant MDV by inserting one or more endogenous or exogenous genes, operably linked to a control element for expression, into a region of the MDV genome comprising the novel nucleotide sequence, wherein the insertion interrupts expression of the open reading frame.

17 Claims, 5 Drawing Sheets

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 1285 nucleotides
( B ) TYPE: nucleic acid
( C ) STRANDEDNESS: single- stranded
( D ) TOPOLOGY: linear ( i i ) MOLECULE TYPE: cDNA ( i i i ) HYPOTHETICAL: yes ( i v ) IMMEDIATE SOURCE:
( A ) LIBRARY: cDNA
( B ) CLONE: clone L1

( v ) ORIGINAL SOURCE:
( A ) ORGANISM: Marek's Disease Virus
( B ) STRAIN: MDCC-CU41
( C ) CELL TYPE: virus ( v i ) FEATURE:
( A ) LOCATION: L1 open reading frame, 725-1045
( B ) IDENTIFICATION METHOD: by experiment
( C ) OTHER INFORMATION:

( v i i ) SEQUENCE DESCRIPTION: SEQ ID NO:1:

ATCGATTTAC TGACATAAAA AAATCCTCTG GGGTAACAAA TTTTCCTTAC 50

CGTGTAGCTT AGACTCGGAA GAACTATTTT GAGTTACATG GTCAGGGGAT 100

TTGTTGGCTC CAGGAGTTCC GAAGTATTAG ATAAACTTAG CTATGTGGAA 150

AACTTCTGGG GCAACATCCC TCGGCCCCAG ACTGCTTAAA TGGCAAATTC 200

TCGTTCTATA CAGAACGGTT GGGGAAGGGG GGGGGGGTAT GGAGTATTAT 250

TCGGGATATG GCTTCTATGA AGCTGCGGTA AGTTTTCCAG GCTCAAAAAC 300

TATGCCTGGC TGTTTTTTTT TTTTTTTTTT TTAGAAGGGA TATGGACATC 350

GCACATTAAG GAATATTAAA GATAACAGGA TGGACATTCG GATGTAAAAG 400

GAATAAGCGA AACCTTTAGC AGATGTGAGT TAATGCAGTC TCGTATAATT 450

-continued

```
CGGTGGTGCT GATTAGGTTA TCGTAAGGAA CAACACGATT GATCTCTCAT 500

CCGCGTCCCA GCAATCAGGC CTATGTCCCT CTCCTGTGGC CAGCTCACTG 550

GCTGTGCACT GTGCGATTCT AAGTGCTACA GTCGTGAGCA GATCAATGGA 600

TCGGGGCTCG CGCAACACTA CTGTAATTAA ATATTCGTTT ATGAATTATG 650

CAAATATGCA CAGATAATAT ATACAGGGAT GCACAGACAT ACTCCTATGC 700

ACCGATACAC AGGCACATAG GCAG ATG TCG ACA TTA ACG AAT ATA 745
                           Met Ser Thr Leu Thr Asn Ile
                            1               5

CAG GCA CGG ACC TCC AGG AAC ATA TGG AAA ATA CCT CAT CGC  787
Gln Ala Arg Thr Ser Arg Asn Ile Trp Lys Ile Pro His Arg
         10                  15                  20

AGA GAC GCT TAT GCA GGA GTA ATC TGC GTT AAG TCG TTA CTG  829
Arg Asp Ala Tyr Ala Gly Val Ile Cys Val Lys Ser Leu Leu
             25                  30                  35

GAT TGT AAC GGC TAT CCG GAG ACT CTC TTC CCC TTT TGC TTG  871
Asp Cys Asn Gly Tyr Pro Glu Thr Leu Phe Pro Phe Cys Leu
                 40                  45

TTC ACT GTG CGG CAT TAT TAC ATT TAC ACC GGT AAT GCT GCG  913
Phe Thr Val Arg His Tyr Tyr Ile Tyr Thr Gly Asn Ala Ala
 50                  55                  60

CAT GAA AGA GCG AAC GGA ACG AGG CTC GTA CGA CAT TAC AAG  955
His Glu Arg Ala Asn Gly Thr Arg Leu Val Arg His Tyr Lys
     65                  70                  75

AAT AGT TTG AAT TCT CGG GAT AAT CTC CCG ATG GCC TCC CCC  997
Asn Ser Leu Asn Ser Arg Asp Asn Leu Pro Met Ala Ser Pro
         80                  85                  90

TTA TGC TTT CTC TAC GAT GTG GCA TTG TTT ACG CGG CAG TGC 1039
Leu Cys Phe Leu Tyr Asp Val Ala Leu Phe Thr Arg Gln Cys
             95                  100                 105

CAC GTG TGAGGGGACG ATCGGGACGG GATCCATTAC GTAAAATTTA     1085
His Val
    107

GATCTTTTGT AGAAATTCAA TTCCCTTCCC CTTTTACTTT GTTTGATGTG  1135

TGCCACTGTT GTACCGATAG TGCCGCGCGT GAAAGAGTGA ACGGGAAGGG  1185

CTTACGTAAA GAACTGTCGG TGCCGGTACG GGGGAAGCTG TAACGCATTT  1235

CGAGTCTTGA TAAAGCAGAG CATGAAATTA AATCGTATCG CTCCTAAAAA  1285
```

( 2 ) INFORMATION FOR SEQ ID NO:2:

( i ) SEQUENCE CHARACTERISTICS:
( A ) LENGTH: 300 nucleotides
( B ) TYPE: nucleic acid
( C ) STRANDEDNESS: single- stranded
( D ) TOPOLOGY: linear ( i i ) MOLECULE TYPE: DNA ( i i i ) SEQUENCE DESCRIPTION: SEQ ID NO:2:

```
ATGGCCTCCC CCTTATGCTT TCTCTACGAT GTGGCATTGT TTACGCGGCA  50

GTGCCACGTG TGAGGGGACG ATCGGGACGG GATCCATTAC GTAAAATTTA 100

GATCTTTTGT AGAAATTCAA TTCCCTTCCC CTTTTACTTT GTTTGATGTG 150

TGCCACTGTT GTACCGATAG TGCCGCGCGT GAAAGAGTGA ACGGGAAGGG 200

CTTACGTAAA GAACTGTCGG TGCCGGTACG GGGGAAGCTG TAACGCATTT 250

CGAGTCTTGA TAAAGCAGAG CATGAAATTA AATCGTATCG CTCCTAAAAA 300
```

-continued ( 2 ) INFORMATION FOR SEQ ID NO:3:

( i ) SEQUENCE CHARACTERISTICS:
( A ) LENGTH: 17 nucleotides
( B ) TYPE: nucleic acid
( C ) STRANDEDNESS: single- stranded
( D ) TOPOLOGY: linear ( i i ) MOLECULE TYPE: DNA ( i i i ) IMMEDIATE SOURCE:
( A ) LIBRARY: synthesized ( i v ) SEQUENCE DESCRIPTION: SEQ ID NO:3:

CAACATAAAG GAAAGGG 17

( 2 ) INFORMATION FOR SEQ ID NO:4:

( i ) SEQUENCE CHARACTERISTICS:
( A ) LENGTH: 17 nucleotides
( B ) TYPE: nucleic acid
( C ) STRANDEDNESS: single- stranded
( D ) TOPOLOGY: linear ( i i ) MOLECULE TYPE: DNA ( i i i ) IMMEDIATE SOURCE:
( A ) LIBRARY: synthesized ( i v ) SEQUENCE DESCRIPTION: SEQ ID NO:4:

CGTAATGGAT CCCGTCC 17

( 2 ) INFORMATION FOR SEQ ID NO:5:

( i ) SEQUENCE CHARACTERISTICS:
( A ) LENGTH: 188 nucleotides
( B ) TYPE: nucleic acid
( C ) STRANDEDNESS: single- stranded
( D ) TOPOLOGY: linear ( i i ) MOLECULE TYPE: DNA ( i i i ) SEQUENCE DESCRIPTION: SEQ ID NO:5:

CCAGCTCACT GGCTGTGCAC TGTGCGATTC TAAGTGCTAC AGTCGTGAGC 50

AGATCAATGG ATCGGGGCTC GCGCAACACT ACTGTAATTA AATATTCGTT 100

TATGAATTAT GCAAATATGC ACAGATAATA TATACAGGGA TGCACAGACA 150

TACTCCTATG CACCGATACA CAGGCACATA GGCAGATG 188

( 2 ) INFORMATION FOR SEQ ID NO:6:

( i ) SEQUENCE CHARACTERISTICS:
( A ) LENGTH: 237 nucleotides
( B ) TYPE: nucleic acid
( C ) STRANDEDNESS: single- stranded
( D ) TOPOLOGY: linear ( i i ) MOLECULE TYPE: DNA ( i i i ) SEQUENCE DESCRIPTION: SEQ ID NO:6:

TCGACATTAA CGAATATACA GGCACGGACC TCCAGGAACA TATGGAAAAT 50

ACCTCATCGC AGAGACGCTT ATGCAGGAGT AATCTGCGTT AAGTCGTTAC 100

TGGATTGTAA CGGCTATCCG GAGACTCTCT TCCCCTTTTG CTTGTTCACT 150

GTGCGGCATT ATTACATTTA CACCGGTAAT GCTGCGCATG AAAGAGCGAA 200

CGGAACGAGG CTCGTACGAC ATTACAAGAA TAGTTTG 237

-continued ( 2 ) INFORMATION FOR SEQ ID NO:7:

( i ) SEQUENCE CHARACTERISTICS:
( A ) LENGTH: 244 nucleotides
( B ) TYPE: nucleic acid
( C ) STRANDEDNESS: single- stranded
( D ) TOPOLOGY: linear ( i i ) MOLECULE TYPE: DNA ( i i i ) SEQUENCE DESCRIPTION: SEQ ID NO:7:

```
CGTTACTGGA TTGTAACGGC TATCCGGAGA CTCTCTTCCC CTTTTGCTTG    50
TTCACTGTGC GGCATTATTA CATTTACACC GGTAATGCTG CGCATGAAAG   100
AGCGAACGGA ACGAGGCTCG TACGACATTA CAAGAATAGT TTGAATTCTC   150
GGGATAATCT CCCGATGGCC TCCCCCTTAT GCTTTCTCTA CGATGTGGCA   200
TTGTTTACGC GGCAGTGCCA CGTGTGAGGG GACGATCGGG ACGG   244
```

( 2 ) INFORMATION FOR SEQ ID NO:8:

( i ) SEQUENCE CHARACTERISTICS:
( A ) LENGTH: 172 nucleotides
( B ) TYPE: nucleic acid
( C ) STRANDEDNESS: single- stranded
( D ) TOPOLOGY: linear ( i i ) MOLECULE TYPE: DNA ( i i i ) SEQUENCE DESCRIPTION: SEQ ID NO:8:

```
GATCCATTAC GTAAAATTTA GATCTTTTGT AGAAATTCAA TTCCCTTCCC    50
CTTTTACTTT GTTTGATGTG TGCCACTGTT GTACCGATAG TGCCGCGCGT   100
GAAAGAGTGA ACGGGAAGGG CTTACGTAAA GAACTGTCGG TGCCGGTACG   150
GGGGAAGCTG TAACGCATTT CG   172
```

( 2 ) INFORMATION FOR SEQ ID NO:9:

( i ) SEQUENCE CHARACTERISTICS:
( A ) LENGTH: 17 nucleotides
( B ) TYPE: nucleic acid
( C ) STRANDEDNESS: single- stranded
( D ) TOPOLOGY: linear ( i i ) MOLECULE TYPE: DNA ( i i i ) IMMEDIATE SOURCE:
( A ) LIBRARY: synthesized ( i v ) SEQUENCE DESCRIPTION: SEQ ID NO:9:

```
CGTAATGGAT CCCGTCC   17
```

( 2 ) INFORMATION FOR SEQ ID NO:10:

( i ) SEQUENCE CHARACTERISTICS:
( A ) LENGTH: 22 nucleotides
( B ) TYPE: nucleic acid
( C ) STRANDEDNESS: single- stranded
( D ) TOPOLOGY: linear ( i i ) MOLECULE TYPE: DNA ( i i i ) IMMEDIATE SOURCE:
( A ) LIBRARY: synthesized ( i v ) SEQUENCE DESCRIPTION: SEQ ID NO:10:

```
AGTAATCTGC GTTAAGTCGT TA   22
```

-continued ( 2 ) INFORMATION FOR SEQ ID NO:11:

( i ) SEQUENCE CHARACTERISTICS:
( A ) LENGTH: 22 nucleotides
( B ) TYPE: nucleic acid
( C ) STRANDEDNESS: single- stranded
( D ) TOPOLOGY: linear ( i i ) MOLECULE TYPE: DNA ( i i i ) IMMEDIATE SOURCE:
( A ) LIBRARY: synthesized ( i v ) SEQUENCE DESCRIPTION: SEQ ID NO:11:

GTAAACAATG CCACATCGTA GA 22

( 2 ) INFORMATION FOR SEQ ID NO:12:

( i ) SEQUENCE CHARACTERISTICS:
( A ) LENGTH: 23 nucleotides
( B ) TYPE: nucleic acid
( C ) STRANDEDNESS: single- stranded
( D ) TOPOLOGY: linear ( i i ) MOLECULE TYPE: DNA ( i i i ) IMMEDIATE SOURCE:
( A ) LIBRARY: synthesized ( i v ) SEQUENCE DESCRIPTION: SEQ ID NO:12:

CATATGTTCC TGGAGGTCCG TGC 23

( 2 ) INFORMATION FOR SEQ ID NO:13:

( i ) SEQUENCE CHARACTERISTICS:
( A ) LENGTH: 29 nucleotides
( B ) TYPE: nucleic acid
( C ) STRANDEDNESS: single- stranded
( D ) TOPOLOGY: linear ( i i ) MOLECULE TYPE: DNA ( i i i ) IMMEDIATE SOURCE:
( A ) LIBRARY: synthesized ( i v ) SEQUENCE DESCRIPTION: SEQ ID NO:13:

ATGAAATTAA ATCGTATCGC TCCTAAAAA 29

MAREK'S DISEASE VIRUS NUCLEOTIDE SEQUENCE AND METHODS OF USE

This application is a continuation-in-part of U.S. patent application Ser. No. 08/180,051 filed Jan. 11, 1994, which is herein incorporated by reference, and which is now abandoned

BACKGROUND OF THE INVENTION

1.1 Field of the Invention

The present invention relates to a novel sequence in the genome of the Marek's disease virus (MDV) which is actively transcribed in MDV-induced lymphoblastoid tumors and tumor cell lines. More particularly, this invention provides methods of use of the novel sequence, or oligonucleotides synthesized to correspond thereto, as reagents in molecular diagnostics directed to the detection of MDV genetic material; and provides methods of use of the novel sequence as a region in the MDV genome which is nonessential for virus replication into which an extra copy of an endogenous (MDV) gene and/or one or more exogenous genes can be inserted for expression from such recombinant viral vector.

1.2 Description of the Background and Related Art

Marek's disease is a lymphoproliferative disease of chickens caused by MDV. MDV, a naturally occurring herpesvirus, infects bursa-derived and thymus-derived lymphocytes in chickens, and may subsequently induce a lymphoma of thymus-derived lymphocytes. Although the MDV genome is present in tumors induced in the MDV-infected chickens, these tumors are generally free of virus particles indicating that latency has been established. MDV-infected chickens may also exhibit neural involvement characterized by nerve paralysis. Since Marek's disease is contagious, the virus has become an important pathogen of chickens, particularly in an environment of large scale breeding such as in the poultry industry.

MDV and herpesvirus of turkey (HVT) are herpesvirus of poultry which are antigenically related. It is generally accepted that MDV and HVT isolates can be divided into three serotypes. Serotype 1 comprises MDV isolates with varying degrees of oncogenic potential; i.e., ranging from isolates that are of high oncogenicity to isolates of lesser oncogenicity. Serotype 2 comprises nononcogenic MDV isolates. Serotype 3 comprises HVT isolates. Monoclonal antibodies have been developed against MDV and HVT with cross-reactive antigenic determinants being observed on MDV and HVT polypeptides. However, differentiation of the three serotypes can be achieved by the ability or lack of ability of the different serotypes to replicate in certain cell lines, and differences in plaque morphology. Thus, for epidemiologic and vaccine purposes, there is a need for a rapid, sensitive, and specific reagent for distinguishing the oncogenic MDV strains (serotype 1) from non-oncogenic MDV strains (serotype 2) and HVT (serotype 3).

Because of a lack of effective therapeutic drugs for treatment of Marek's disease, approaches to prevent the disease have focused on vaccine development. One such vaccine, described in U.S. Pat. No. 4,160,024, involves a strain of MDV which is naturally nonocogenic and unattenuated. Another vaccine, disclosed in U.S. Pat. No. 4,980,162, is a combined vaccine consisting of cultured cells infected with an attenuated infectious laryngotracheitis virus, and cultured cells infected with attenuated MDV or herpesvirus of turkey (HVT). A process for preparing a plasmid vector which contains the MDV Type I BamHI fragment, into which is incorporated a structural gene encoding an exogenous protein, is disclosed in U.S. Pat. No. 5,171,677.

Currently, Marek's disease is controlled by vaccination of embryos at 17–19 days of incubation, or one day old chicks with either HVT; serotype 2 strains of MDV; attenuated (of low pathogenicity) and/or nononcogenic strains of MDV serotype 1, or combinations thereof. However, recently vaccination breaks have been reported in chickens vaccinated with the bivalent vaccine consisting of serotype 2 MDV or HVT (R. L. Witter in *Proceedings XIX World's Poultry Congress*, Amsterdam, The Netherlands, 1992, 1:298–304), suggesting that new approaches are needed to control Marek's disease. Increased virulence of MDV isolates, decreased genetic resistance of chicken stocks, immunosuppression by other microbial pathogens, and poor management of vaccination procedures may be factors which have contributed to recent vaccination breaks.

To provide for MDV as a vector and vaccine against Marek's Disease, it is desirable to locate a site within the MDV genome which is not essential for viral replication and function; and into which can be inserted one or more endogenous genes encoding an MDV antigen(s) to further stimulate the immune response against the encoded antigen (s). To provide for MDV as a viral vector or as an expression vector for use as a multivalent vaccine, it is desirable to locate a site within the MDV genome which is not essential for viral replication and function; and into which can be inserted one or more exogenous genes encoding an antigen (s) of a poultry pathogen other than MDV to further stimulate the immune response against MDV and such other poultry pathogens. Alternatively, a combination of copies of endogenous genes and exogenous genes may be inserted into a nonessential region of such viral vector.

SUMMARY OF THE INVENTION

A novel sequence, comprising an open reading frame (ORF), has been identified in the MDV genome. RNA transcripts from this sequence have been detected in Marek's disease tumor cell lines, which have a limited number of MDV-specific transcripts. In addition, this transcript is only one of two MDV-specific transcripts in a reticuloendotheliosis virus (REV)-transformed lymphoblastoid cell line latently-infected with MDV (Pratt et al., 1992, *J. Virol.* 66:7239–7244). This transcript can also be detected in spleen cells obtained from chickens latently-infected with MDV (unpublished data). Only a low, but detectable, rate of transcription from this sequence occurs in lyrically-infected cells. The novel sequence of the present invention is nonessential for virus replication, and therefore can be used as a region for insertion and expression in MDV of other endogenous (MDV) genes or exogenous genes.

Accordingly, one object of the present invention is to provide a novel nucleotide sequence of serotype 1 MDV which can be used to distinguish serotype 1 MDV from serotype 2 and HVT.

Another object of the present invention is to provide novel nucleotide sequence of serotype 1 MDV which represents a region in the MDV genome, wherein the region is nonessential for virus replication and function, and into which an extra copy(s) of an endogenous (MDV) gene and/or exogenous gene can be inserted for expression from this recombinant viral vector.

Another object of the present invention is to provide a process for producing recombinant MDV as a viral vector.

A further object of the present invention is to provide for a multivalent vaccine for expression of genes in birds using a recombinant MDV as a viral vector.

Other objects and advantages of the invention will become readily apparent from the ensuing description.

DETAILED DESCRIPTION OF THE INVENTION

The MDV genome is a linear 180 kilobase pair double stranded molecule consisting of two unique regions: a unique short region (US), and a unique long region (UL). Each of the unique regions is flanked by inverted repeats: a long terminal repeat (TRL) and internal long inverted repeat (IRL) for UL, and a short internal inverted repeat (IRS) and short terminal repeat (TRS) for US (FIG. 1).

Presently, the transformation process of T-cells by MDV is poorly understood. In lymphoblastoid cell lines established from Marek's disease tumors, viral gene expression is very limited whereas many viral transcripts are found in lyrically infected cells (Silver et al., 1979, *Virology* 93:127–133). For example, at least 66 discrete transcripts were detected by Northern blot analysis of lytically-infected chicken embryo fibroblasts (CEF), whereas less than 8 transcripts were detected in lymphoblastoid cell lines (Schat et al., 1989, *Int. J. Cancer* 44:101–109). This observation suggests that MDV oncogenicity and latency are closely related, and that the few transcripts found in Marek's disease tumors, and their corresponding gene products, may be important for the initiation and/or maintenance of latency and/or tumor cell development by MDV. Recent studies by Schat et al. (1989, supra) and Sugaya et al. (1990, *J. Virol.* 64:5773–5782) demonstrated that the regions actively transcribed in tumor cell lines are the US and IRS regions, which correspond to the BamHI-H, -$I_2$, -L, and -A DNA fragments according to the restriction enzyme map of MDV (Fukuchi et al., 1984, *J. Virol.* 51:102–109).

Although it is known that the BamHI-L region of the MDV genome is actively transcribed in MDV-induced lymphoblastoid tumors and tumor cell lines, information is lacking about the identification and characterization within that region of sequence(s), and their corresponding gene products, associated with the initiation and/or maintenance of tumor cell development. Additionally, there is a lack of information as to the identification and characterization of MDV transcripts in latently-infected cells of chickens.

Figure 1:
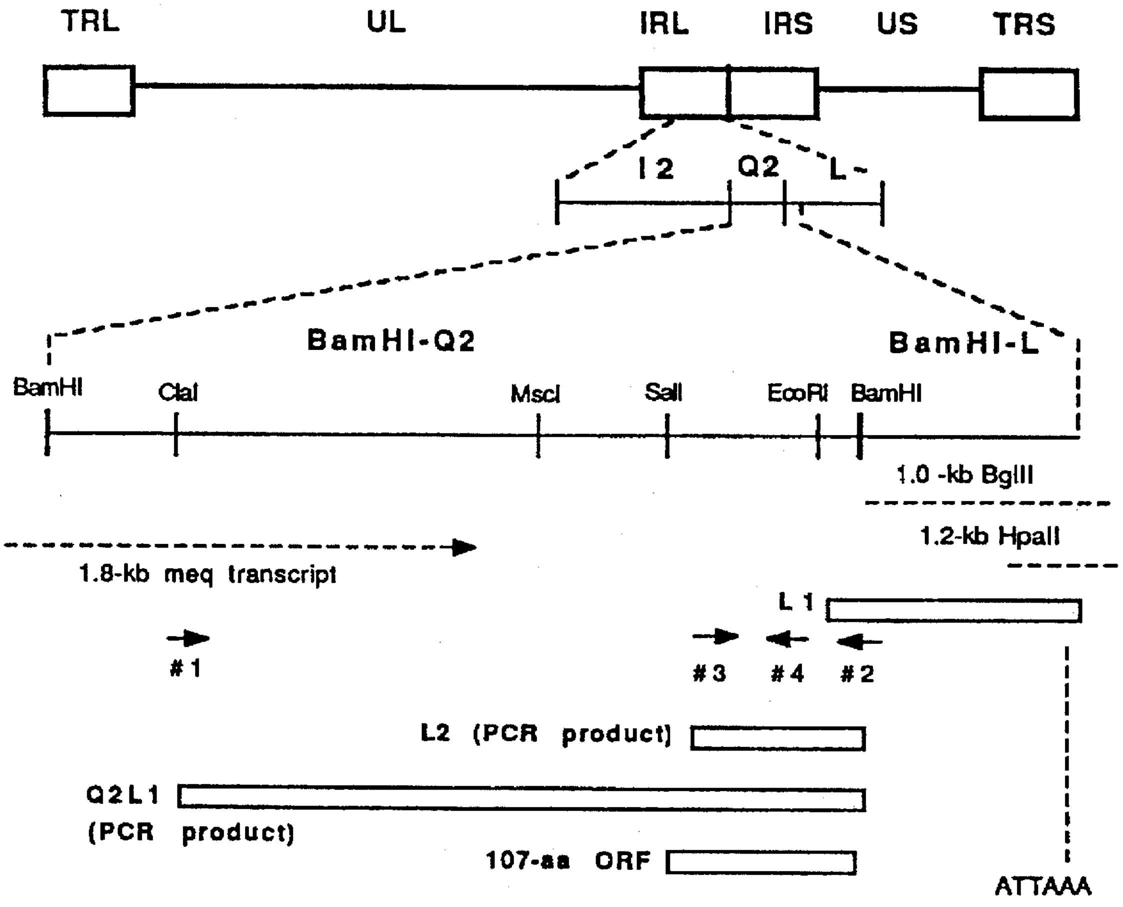
FIG. 1 is a schematic representation of the genomic structure of MDV with restriction map positions of BamHI-$I_2$,-$Q_2$, and -L regions; and a restriction enzyme map of the BamHI-$Q_2$ region and part of the BamHI-L fragment with locations of BamHI-L-specific cDNA clones (L1 and L2). Locations of the L1 and L2 cDNA clones, the Q2L1 PCR product, and an open reading frame encoding 107 amino acids are shown as open boxes. Locations of the 1.8-kb meq transcript, and the 1.0 kb BglII and 1.2-kb HpaII subfragments of the BamHI-L fragment, are shown as broken lines. The location of the polyadenylation signal (ATTAAA) in L1 clone is also shown.
Figure 2:
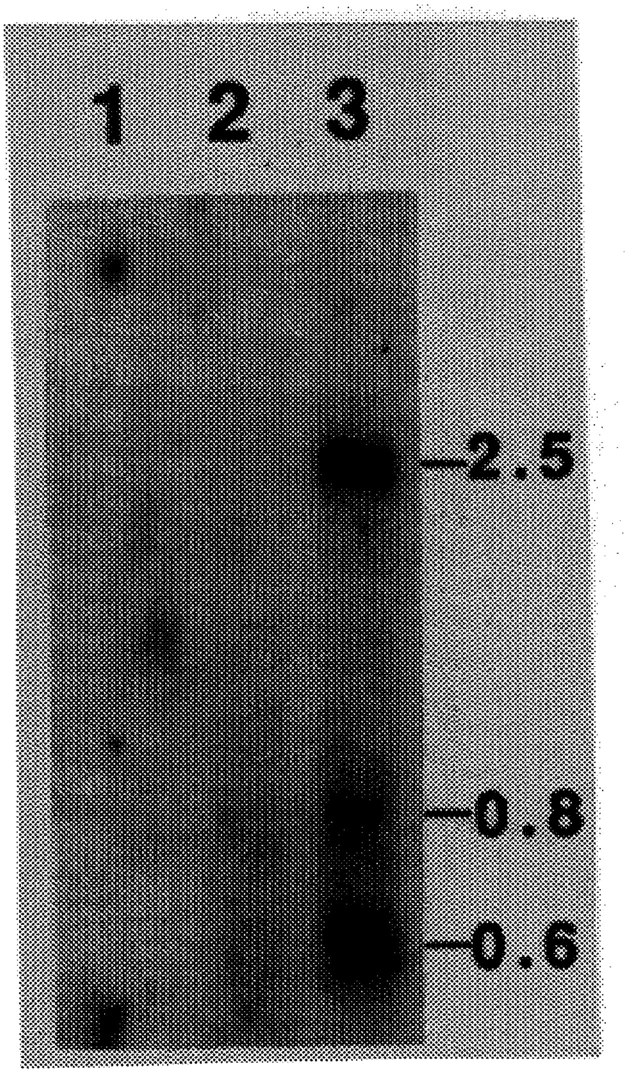
FIG. 2 represents Northern blot analysis to confirm the origins of the L1 cDNA clone. Poly(A)$^+$ RNA isolated from either uninfected chicken kidney cells (CKC) (lane 1), RB1B-infected CKC (lane 2), or CU41 (lane 3) was hybridized with a probe prepared from the L1 cDNA clone. Sizes of transcripts are shown in kilobases.

The present invention relates to the identification and characterization of a novel nucleotide sequence which originates in the BamHI-$Q_2$ region and ends in the BamHI-L region of the short inverted internal repeat (IRS) of the MDV genome, as represented in FIG. 1. A cDNA clone ("L1 cDNA clone") containing a portion of this novel nucleotide sequence was isolated from a cDNA library prepared from a Marek's disease lymphoblastoid cell line, MDCC-CU41 (CU41; Ohashi et al., 1992, pp. 54–57 in *Proceedings 19th World Poultry Congress*). CU41 is a non-expression cell line which contains none or only a few cells expressing viral antigens. L1 transcripts are expressed in relatively higher amounts in the Marek's disease lymphoblastoid cell line CU41 (FIG. 2, lane 3) than in lytically infected cells (FIG. 2, lane 2). From the DNA sequence of the L1 cDNA clone, and from the surrounding nucleotide sequences in the genome of oncogenic MDV, one open reading frame ("L1 ORF") of about 321 nucleotides was identified which can encode 107 amino acids (see SEQ ID NO:1). Moreover, L1 transcripts have also been detected in CU210, a T cell lymphoblastoid cell line developed by transformation with reticuloendotheliosis virus (REV) which was then latently infected with MDV, but not detected in the parent REV cell line free of MDV. Thus, the L1 ORF, and its corresponding gene product of 107 amino acids ("L1"), may be associated with initiation and maintenance of tumor cell development and/or establishment of latency of MDV-infected cells.

Because of the lack of effective drugs to therapeutically treat chickens with Marek's disease, and with recent reports of vaccination breaks in chickens vaccinated with virus, alternative approaches to controlling Marek's disease should be considered. One embodiment of the present invention is to use the L1 ORF and/or surrounding sequences depicted in the 1285 nucleotide sequence of SEQ ID NO:1 as an insertion site capable of incorporating one or more endogenous and/or exogenous genes. Suitable restriction sites, as shown in FIG. 1, are contained within the novel nucleotide sequence which can be used as an insertion site.

This embodiment involves the development of a Marek's disease virus which lacks oncogenicity. As noted in U.S. Pat. No. 4,160,024 to Schat et al., which patent is assigned to the assignee of the present invention and is incorporated herein by reference, unattenuated pathogenic strains of MDV have been unacceptable as vaccines for poultry because of their oncogenic potential. While regions within the MDV genome have been proposed for use as an insertion site (P. Bandyopadyay et al., 1987, 12th International Herpesvirus Workshop; Sakaguchi et al., European Patent Application Publication No. 0 522 535 A1, 1993), there has not been disclosed the use of a region which appears to be associated with initiation and maintenance of tumor cell development in MDV-infected cells. Thus, it is desirable to use a region in the MDV genome as an insertion site which is nonessential to virus replication, and the interruption of which may result in inhibition of the ability to initiate latency or tumor cell development in MDV-infected cells. Further, it may be desirable to use a region contained within a repeated sequence of the MDV genome, as this can provide an additional insertion site.

In one variation of this embodiment, the L1 ORF of an unattenuated pathogenic strain of MDV (serotype 1) can be genetically engineered not to express the L1 protein by using the L1 ORF, or the surrounding sequences controlling its expression, as an insertion site. For example, since the L1ORF appears non-essential for virus replication, expression of the L1 protein can be interrupted by the insertion of one or more endogenous and/or exogenous sequences into the L1 ORF, resulting in a recombinant MDV that is inhibited in its oncogenicity and can be used as a vector in a multivalent vaccine. An exogenous gene would encode protein which acts as an effective antigen in inducing a protective immune response against its corresponding organism of origin. Thus, the recombinant MDV could serve as a combined vaccine against Marek's disease and against other diseases of poultry. In another variation of this embodiment, instead of using the insertion site to insert an exogenous gene encoding an antigen for vaccination purposes, the inserted exogenous gene encodes a protein which is beneficial to the health and/or growth of poultry infected with such recombinant MDV. Such proteins include, for purposes of illustration but not limitation, growth factors, hormones, cytokines, enzymes, and peptides having antimicrobial or antiviral activity.

In another variation of this embodiment, one or more copies of an endogenous gene, whose gene product is an antigen capable of eliciting a protective immune response, can be inserted within the L1ORF or the surrounding sequences controlling its expression, thereby interrupting L1 production but allowing increased expression of the endogenous gene encoding an MDV antigen for vaccine purposes. For example, glycoprotein B (gB) is a major glycoprotein produced by MDV, which when inoculated into chickens results in the production of neutralizing antibody. Multiple copies of the gene encoding gB can be inserted in the L1 ORF, or the surrounding sequences controlling its expression, to make a more effective recombinant vaccine against Marek's disease. In another variation of this embodiment, instead of using the insertion site to insert an endogenous gene encoding an antigen for vaccination purposes, the inserted endogenous gene encodes a protein which is beneficial to the health and/or growth of poultry infected with such recombinant MDV. Such endogenous proteins include, for purposes of illustration but not limitation, species-specific growth factors, hormones, cytokines, enzymes, and peptides having antimicrobial or antiviral activity.

EXAMPLE 1

Isolation and Characterization of the L1 ORF

The L1 ORF is a sequence derived from the sequence of an MDV-specific cDNA clone, L1 cDNA clone which was obtained through screening of the CU41 cDNA library with the gel-purified BamHI-L fragment as a probe; and enzymatic amplification of a MDV genomic fragment "Q2L1", as shown in FIG. 1. CU41, a Marek's disease lymphoblastoid cell line established from a RB1B-induced tumor (MDV strain RB1B is a very highly oncogenic strain described previously by Schat et al., 1982, *Avian Pathol.* 11:593–605), is a non-expression cell line which contains none or only a few cells expressing viral antigens (Calnek et al., 1981, *Infect. Immun.* 34:483–491). CU41 was selected for making the cDNA library because only six MDV-specific transcripts, including a 0.6-kb BamH1-L transcript, were detected in this cell line (Schat et al., 1989, supra). For the isolation of L1 cDNA clone, a cDNA library was prepared from the poly $(A)^+$ RNA obtained from CU41 cells. The library was screened by plaque hybridization with a $^{32}P$-labeled MDV (strain GA) BamHI-L fragment, and the hybridizing phages were plaque-purified. Subsequent in vivo excision and rescue of pBluescript (SK)™ carrying cDNA inserts were performed.

Southern blot analysis was performed to determine the approximate map position of the L1 cDNA clone. The BamHI-L fragment was digested by BglII, fractionated on a 1.2% agarose gel, and transferred to a nylon hybridization membrane. In a separate restriction, the BamHI-L fragment was digested with HpaII, fractionated on a 1.2% agarose gel, and transferred to a nylon membrane. $^{32}P$-labeled probes were prepared by using gel-purified cDNA inserts as templates, and hybridizations with the membranes were performed. As shown in FIG. 1, from Southern blot analysis it was determined that the L1 cDNA clone hybridized with a 1.0 kb BglII subfragment and a 1.2 kb HpaII subfragment of the BamHI-L fragment. By aligning the subfragments with the restriction map of the BamHI-L fragment, the exact location of the subfragments could be determined, as shown in FIG. 1. The 3' end of the L1 clone was localized at 221 bases to the right of the left BamHI site of the BamHI-L fragment.

In order to characterize the transcripts coded for by L1, a radiolabeled probe (SEQ ID NO:2) was prepared from the L1 cDNA clone, and used for Northern blot analysis. In this experiment, total cellular RNA was isolated from uninfected chicken kidney cells (CKC), RB1B-infected CKCs, and CU41 using the method of Chomczynski et al. (1987, *Anal. Biochem.* 162:156–159). Poly$(A)^+$ RNA, purified from the total cellular RNA preparations, were used in the Northern blot analysis. For Northern blotting, 2 μg of each of the poly$(A)^+$ RNA fractions were fractionated by electrophoresis in 1.2% agarose gel containing 2.2M formaldehyde (15), and blotted onto nylon membranes. RNA blots were prehybridized for 3 hours at 42° C. in 50% formamide, 5×SSPE, 5×Denhardt's solution, 0.1% SDS and 100 μg/ml denatured salmon sperm DNA. Hybridization was performed for 18–20 hours at 42° C. in the same solution with addition of the radiolabeled L1 probe (SEQ ID NO:2). After hybridization, the membranes were washed twice with 2×SSPE containing 0.5% SDS at 65° C. for 60 minutes. The hybridized filters were autoradiographed at −80° C. with x-ray film and intensifying screens. The results of the Northern blot analysis of the poly$(A)^+$ RNA fractions from the uninfected CKC, the RB1B-infected CKC, and CU41, are shown in FIG. 2. Three L1-specific transcripts of 2.5 kb, 0.8 kb, and 0.6 kb were detected. The amounts of these transcripts appear to be relatively more abundant in the RNA sample of CU41 than in that of RB1B-infected CKC. The L1 probe (SEQ ID NO:2) did not hybridize with the RNA sample from uninfected CKC. Previous studies of MDV-transcripts coded for by the BamHI-L region in CU41 indicated the existence of a 0.6 kb transcript (Schat et al., 1989, supra).

The L1 cDNA clone was subcloned into pBluescript KS(+)™ and sequenced using the dideoxysequencing method. The sequence of the L1 cDNA clone is shown as SEQ ID NO:2. In addition, a 1070-bp ClaI-BamHI fragment ("Q2Li") derived from enzymatic amplification, corresponding to the upstream region of the L1 cDNA clone, was also sequenced. The enzymatic amplification comprised polymerase chain reactions, carried out to amplify a genomic fragment in the BamHI-Q2 region, performed using a standard procedure. The two primers used, #1 (5'-CAACAT AAAGGAAAGGG-3'; SEQ ID NO:3) and #2 (5'-CGTAATGGATCCCGTCC-3'; SEQ ID NO:4), were designed from sequence data of the EcoRI-Q fragment (Jones et al., 1992, supra) and the L1 cDNA clone, respectively. The locations of the primers are shown in FIG. 1. The amplified fragment, Q2L1, was then digested with both ClaI and BamHI, and cloned into pBluescript KS(+)™, and used for DNA sequencing. The nucleotide sequences of the L1 cDNA clone and Q2L1 were aligned, as represented in FIG. 1.

Analysis of the sequences resulted in identification of one ORF, L1 ORF, which can encode a predicted polypeptide of 107 amino acids, L1 (FIG. 1 , nucleotides 725–1045, SEQ ID NO:1). The calculated molecular weight of the L1 polypeptide is 12,385 dalton. The potential translation initiation site (ATG) of the L1 ORF was located at positions 725–727. A 237-base 3' untranslated sequence was present in the cDNA, and a putative poly(A) signal, ATTAAA, was present at positions 1262–1267.

DNA sequence analysis of the 5' upstream region of the cDNA clones resulted in identification of two potential TATA box-like sequences. These are TATAATT at positions 444–450, and TAATATATA at positions 665–673 (of SEQ ID NO:1), from which the length of the predicted transcripts are approximately 0.8 and 0.6 kb without poly(A) tails respectively. Both of these two TATA elements are located downstream of the polyadenylation signal (AATAAG, positions 402–407) for the 1.8-kb meg transcript. Furthermore, some potential transcriptional regulatory sequences were also identified in the region adjacent to the L1 ORF. An Oct-1 binding motif (ATGCAAAT) was found at positions 648–655 (of SEQ ID NO:1). In addition, three copies of similar sequences, ATGCACAGA (positions 656–664, and 679–687; of SEQ ID NO:1), and ATGCACCGA (positions 679–687; of SEQ ID NO:1), were also found near that motif.

Figure 4:
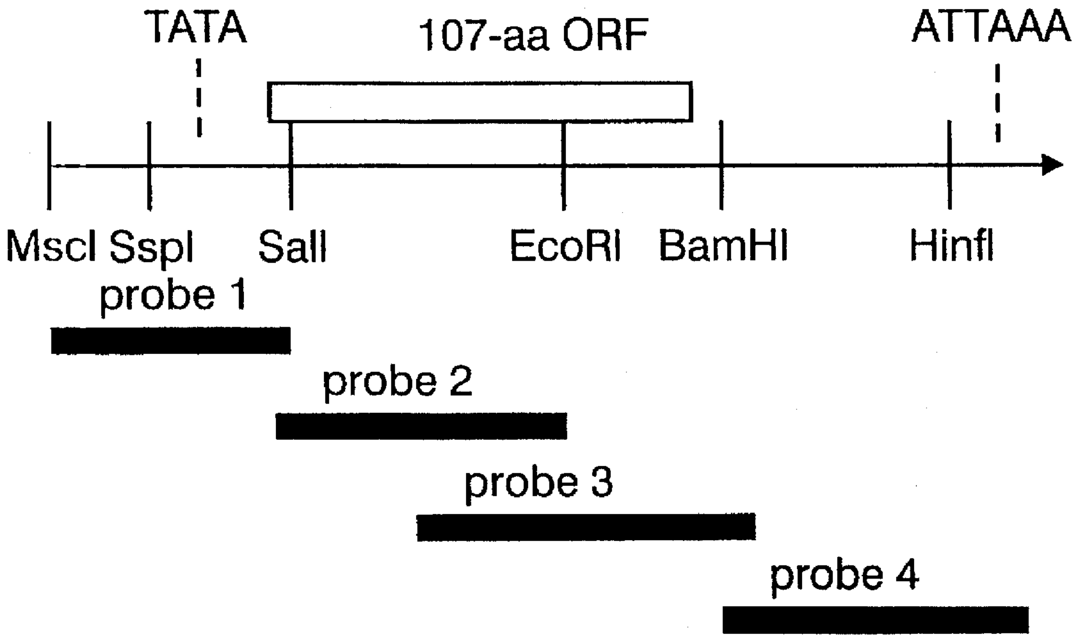
FIG. 4 is a schematic representation showing the locations of the four probes used in the RNase protection assay.

To map the 5' end(s) of the L1 transcripts, RNase protection assays were performed with four different probes (SEQ ID NOs: 5–8) which covered the predicted L1 transcription unit and its upstream region, as shown in FIG. 4. Several subclones were obtained by cloning restriction enzyme-digested cDNA and amplified products from polymerase chain reactions into pBluescript (KS)™. Using these subclones as templates, $^{32}$P-labeled antisense RNA probes were synthesized with either T3 or T7 RNA polymerase. Each of these probes ($3\times10^5$ cpm) was annealed to a total RNA sample (50 μg) prepared from either CU41, CU197 (a reticuloendotheliosis-transformed T lymphoblastoid cell line), RB1B-infected CKC, or uninfected CKC for 18 hours at 42° C., and then digested with RNase. Protected fragments were resolved on 6% polyacrylamide-8M urea sequencing gels and detected by autoradiography.

In this determination of 5' end of the 0.6-kb L1 transcript, some undigested probes were present due to incomplete digestion by RNase after hybridization. However, it was clear from this determination that these four probes (SEQ ID NOs:5–8) specifically hybridized with RNAs from CU41 and RB1B-infected CKC, but not with those from uninfected CKC and CU197. The 514 base SalI-HinfI region is covered by probes 2, 3, and 4 (SEQ ID NOs: 6–8). This region, which corresponds to the L1 ORF and 3' noncoding region of the L1 cDNA clone, was fully protected when hybridized with the RNA sample from either CU41, or RB1B-infected CKC. In addition to a fully protected 193-base fragment, smaller fragments of two different sizes (115, and 42 bases) were detected when the probe 1 (SEQ ID NO:5), corresponding to the MscI-SalI fragment, was hybridized with the RNA sample from either CU41, or RB1B-infected CKC. According to DNA sequence data, a TATA box-like sequence was localized 55 bases upstream of the SalI site, and the predicted length of an unspliced transcript from this TATA box is approximately 600 bases; this agrees with the result of Northern blot analysis. The Northern blot analysis for the RNase protection assays confirmed the observation in the Northern blot analysis used to characterize the transcripts coded for by L1 cDNA, in that the amount of the L1 transcripts were higher in CU41 than in lytically infected CKC.

EXAMPLE 2

Figure 5:
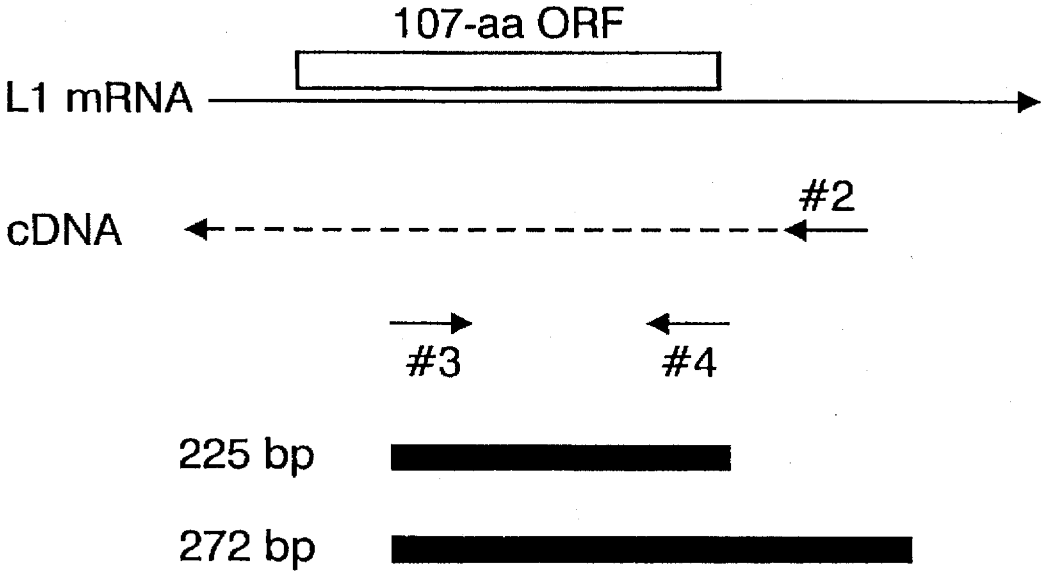
FIG. 5 is a schematic representation showing the locations of primers #2, #3, and #4 used in the reverse transcriptase-polymerase chain reaction for determining L1 transcript expression. Also shown are the size of the predicted amplified fragments.

Further characterization of L1 Expression in Lytically or Latently Infected Cells Reverse transcription-polymerase chain reaction was done to determine whether the L1 transcript is expressed in CU41, an RB1B-transformed non-expression lymphoblastoid cell line, and CU210, an reticuloendothelial virus-transformed cell line latently infected with MDV (Pratt et al., 1992, J. Virol. 66:7239–7244). CU197, a reticuloendotheliosis-transformed T lymphoblastoid cell line, was used as a control for this determination. The reverse transcriptase-polymerase chain reaction was carried out using a commercially available kit and by following the protocol provided by the manufacturer. After treatment with DNase, 1 μg of total RNA prepared from CU41, CU197 and CU210 were reverse-transcribed with primer #2 (SEQ ID NO:9; as schematically represented in FIG. 5). Primers used for subsequent PCR amplification of the cDNA were primer #3 (5'-AGTAATCTGCGTTAAGTCGTTA-3'; SEQ ID NO:10), and primer #4 (5' GTAAACAATGCCACATCGTAGA-3'; SEQ ID NO:11). The amplified fragments were resolved in 2.0% agarose gel, and analyzed by Southern blotting.

Figure 6:
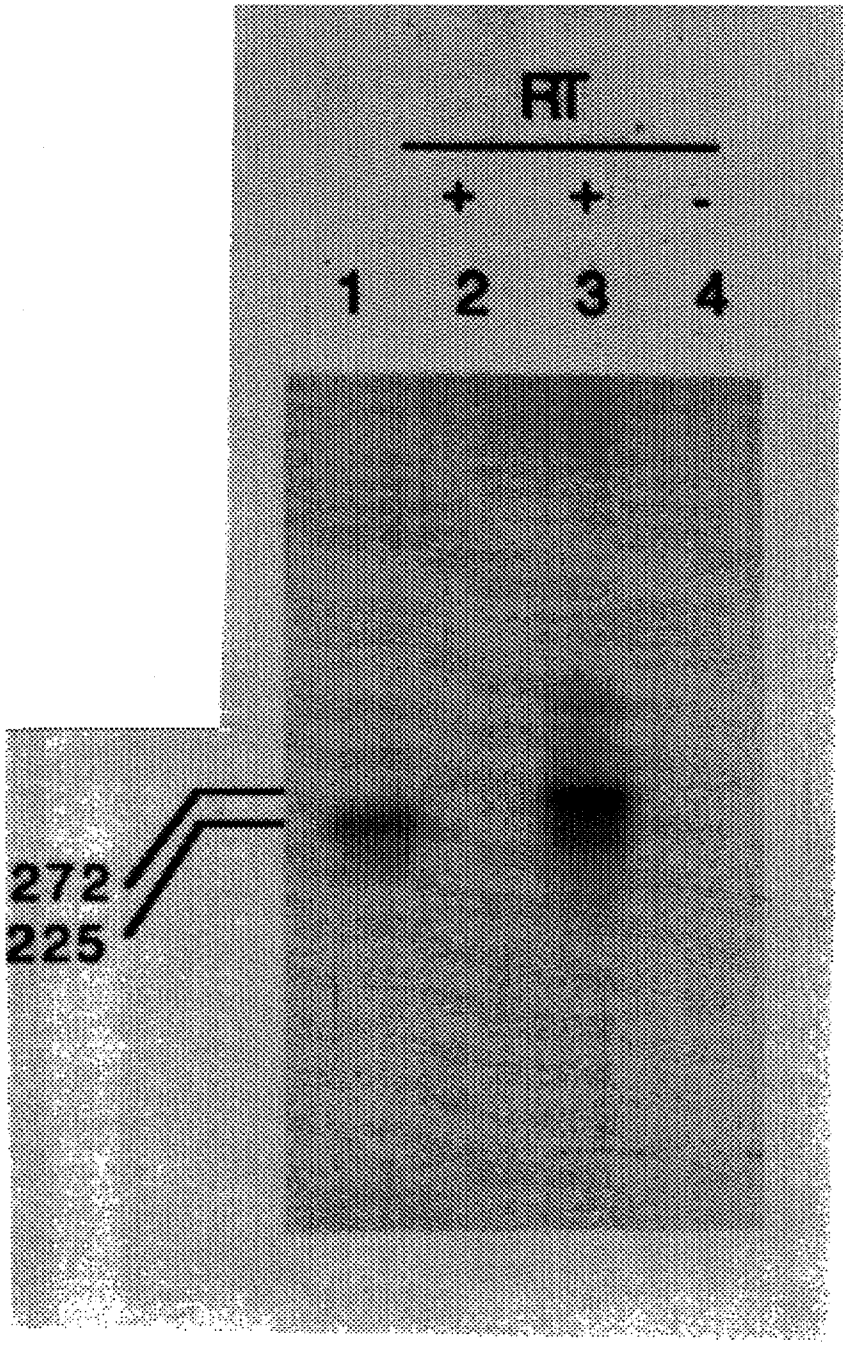
FIG. 6 represents Southern blot hybridization analysis of an amplified product derived from total DNA of CU41 using primers #3 and #4 (lane 1), and reverse-transcriptase polymerase chain amplified products derived from CU197 (lane 2) and CU210 (lane 3), using primers 3 and 4. Lane 4 represents the result of enzymatic amplification of RNA prepared from CU210 (no reverse transcription). The presence or absence of reverse transcriptase in the experimental reactions is indicated at the top of the panel. The sizes of amplified products are shown in base pairs.

Amplification with primers 3 and 4 resulted in an amplified 225 bp fragment located within the L1 ORF (in SEQ ID NO:1) from CU41 (FIG. 6, lane 1) and CU210 (FIG. 6, lane 3), but not from the control cell line CU197 (FIG. 6, lane 2). An additional 272-bp fragment was also amplified in the same reaction as noted in FIG. 6, lane 3. Since not only the 225 bp band but also 272-bp were hybridized with the L1 probe (SEQ ID NO:2), it was concluded that the 272-bp fragment was generated due to the amplification between the primer #3 (SEQ ID NO:10), and primer #2 (SEQ ID NO:9) which was used for reverse transcription and coexisted during this reaction. No DNA was amplified in RNA from CU197, and RNA from CU210 in the absence of reverse transcriptase. These results indicate that the L1 transcript is expressed in cells which are transformed with MDV, and cells latently infected with MDV.

Using methods and materials according to Example 1, chickens lyrically infected, and chickens latently infected, with MDV were analyzed for the presence of L1 transcripts in their spleen cells. N-2a chickens were infected at 3 weeks of age with MDV strain GA-5. At various days post infection (DPI), birds were analyzed by harvesting spleen cells, isolating RNA samples, and treating the RNA with RNAse-free DNAse to remove contaminating DNA. Reverse transcriptase polymerase chain reactions (RT-PCR) were performed using different sets of primers to amplify cDNA from different immediate early gene transcripts comprising L1, meq, $PP_{38}$, BamHI-H family ("Hf"), and $ICP_4$. Table 1 shows that L1 transcripts can be detected in lytically-infected chickens (5–9 DPI), and in latently-infected chickens (12–14 DPI).

Table 2 is the same protocol of RT-PCR except that reverse transcriptase was omitted in the experimental design to confirm that the results in Table 1 represents amplified cDNA rather than amplified DNA from contaminating DNA still present in the sample. Expression from late genes is currently under investigation.

TABLE 1

Transcription From Immediate Early Genes In The Infection Process AE Detected By RT-PCR

| DPI | # of birds | virus | Number of Positives L1 | meq | $PP_{38}$ | Hf | $ICP_4$ |
|---|---|---|---|---|---|---|---|
| 5 | 5 | + | 2/5 | 2/5 | 5/5 | 5/5 | 2/5 |
| | 2 | − | 0/2 | 0/2 | 1/2* | 0/2 | 0/2 |
| 9 | 5 | + | 5/5 | 5/5 | 5/5 | 5/5 | 4/5 |
| | 1 | − | 0/1 | 0/1 | 1/1* | 0/1 | 0/1 |
| 12 | 5 | + | 4/5 | 5/5 | 5/5 | 5/5 | 4/5 |
| | 1 | − | 0/1 | 0/1 | 0/1 | 0/1 | 0/1 |
| 14 | 5 | + | 2/5 | 4/5 | 4/5 | 4/5 | 1/5 |
| | 1 | − | 0/1 | 0/1 | 0/1 | 0/1 | 0/1 |
| + control(RNA of CU41) | | | + | + | + | + | + |
| − control | | | − | − | − | − | − |

*probably contamination of RNA or non-specific reaction

TABLE 2

PCR Control Experiment (without RT) In Analyzing Transcription From Immediate Early Genes In The Infection Process

| DPI | # of birds | virus | Number of Positives L1 | meq | $PP_{38}$ | Hf | $ICP_4$ |
|---|---|---|---|---|---|---|---|
| 5 | 5 | + | 0/5 | 0/5 | 0/5 | 0/5 | 0/5 |
| | 2 | − | 0/2 | 0/2 | 0/2 | 0/2 | 0/2 |
| 9 | 5 | + | 0/5 | 0/5 | 0/5 | 0/5 | 0/5 |
| | 1 | − | 0/1 | 0/1 | 0/1 | 0/1 | 0/1 |
| 12 | 5 | + | 0/5 | 0/5 | 0/5 | 0/5 | 0/5 |
| | 1 | − | 0/1 | 0/1 | 0/1 | 0/1 | 0/1 |
| 14 | 5 | + | 0/5 | 0/5 | 0/5 | 0/5 | 0/5 |
| | 1 | − | 0/1 | 0/1 | 0/1 | 0/1 | 0/1 |
| + control(DNA of CU41) | | | + | + | + | + | + |
| − control | | | −* | − | − | − | − |

an additional negative control for L1 included RNA from CU41

EXAMPLE 3

Inhibition of latency and/or tumor cell development in MDV-infected cells

This embodiment of the present invention is to control the development of Marek's disease by inhibiting latency and/or tumor cell development in MDV-infected cells using an antisense ap- proach. Viral latency and transformation are known to be intimately related in MDV. It has been reported that a 0.6-kb BamHI-L-specific transcript (one of only two MDV-specific transcripts detected from CU210), is expressed in a relatively high amount in CU210, an REV-transformed cell line latently infected with MDV (Pratt et al., 1992, supra). The data presented in Example 1 clearly show that CU210 expresses the origin of the L1 and cDNA clone, and the size of the L1 transcript is 0.6-kb. Thus, the L1 transcript appears to be associated with MDV latency in tumor cells. Further support for this association are the findings, presented in Examples 1 & 2, that a) L1 transcripts are more abundant (high level of transcription) in the MDV-transformed cell line CU41 than in lyrically infected cells (low level of transcription); b) a high level of L1 transcripts are also detected in cells latently-infected with MDV, as evidenced by analysis of CU210; and c) L1 transcripts have been detected by Northern blot analysis of RNA from chicken spleen cells latently-infected with MDV.

In this approach to inhibiting latency and/or tumor cell development in MDV-infected cells, sequences antisense to the L1 ORF, or alternatively to L1 ORF transcripts, can be introduced into cells of chickens or chick embryos. Using the methods according to Example 1, or other methods known in the art such as oligonucleotide synthesis, sequences can be produced that are antisense to the L1 ORF, or alternatively to L1 ORF transcripts. An antisense sequence is defined as a complementary strand to the target strand or sequence (i.e. wherein the nucleotide sequence is inverted in order to its complementary bases) such that the antisense sequence can hybridize to the target sequence under conditions known to those skilled in the art. In this embodiment, the antisense sequence may be a nucleotide sequence of 10 bp or greater which hybridizes to the L1 ORF, or to its corresponding upstream sequences involved in the regulation and initiation of transcription, wherein hybridization blocks transcription from the L1 ORF. Such sequences are readily apparent to those skilled in the art from the sequence of the L1 ORF and its corresponding upstream regulatory regions disclosed in SEQ ID NO:1. Similarly, antisense RNA can be produced to effect sequence-specific inhibition of translation from the L1 ORF transcripts.

In one variation of this embodiment, antisense to L1 ORF, or alternatively to L1 ORF transcripts, can be injected directly into the tissue of chickens, or embryos between 17 and 21 days of incubation. A requirement of this variation is that the antisense must be capable of penetrating the tissue cell membranes so as to effect hybridization to its L1-specific target sequence in an MDV-infected cell and consequently inhibit viral function. In this respect, antisense oligonucleotides, such as phosphodiester oligos, have been demonstrated to be internalized by cells and subsequently exhibit inhibition of viral function (Stein et al., 1993, *Science* 261:1004–1012).

In another variation of this embodiment, using methods known to those skilled in the art, the L1 ORF sequence can be inserted in an antisense direction into any virus vector useful as a vaccine, wherein transcription of antisense RNA from the ORF is under the control of a constitutive promoter. This recombinant viral vaccine vector can either be inoculated into embryos in ovo or into chicks directly after hatching. In yet another variation of this embodiment, using methods known to those skilled in the art, sequences which can be transcribed to antisense to L1 ORF transcripts are inserted into a plasmid vector. The plasmid vector is constructed to have an origin of replication such as from SV40, and a eukaryotic promoter or transcriptional control elements such as an MDV promoter or other viral transcriptional control elements known in the art. The recombinant plasmid is constructed such that in vivo transcription into antisense is regulated by either an inducible promoter or a constitutive promoter. The recombinant plasmid is then injected into embryos in ovo or into chicks directly after hatching. Direct gene transfer into animals resulting in expression of the exogenous gene in vascular endothelial cells, as well as the tissue of the major organs, has been demonstrated by techniques in the art such as by injecting intravenously an expression plasmid:cationic liposome complex (Zhu et al., 1993, *Science* 261:209–211). Other effective methods for delivering vector DNA into a target cell are known in the art. In one example, purified recombinant plasmid DNA containing viral genes has been used to inoculate (whether parentally, mucosally, or via gene-gun immunization) chickens to induce a protective immune response (Fynan et al., 1993, *Proc. Natl. Acad. Sci. USA* 90:11478–11482). In another example, cells removed from the chick or embryo can be transfected or electroporated by standard procedures known in the art, resulting in the introduction of the vector DNA into the target cell. Cells containing the vector DNA may be selected from those lacking the vector DNA by incorporating a selection marker into the vector such as the neo gene, and growing the cells in the corresponding selection media such as in the presence of G418. Selected cells, containing the recombinant expression vector for expressing antisense to L1 ORF transcripts, may then be reintroduced into the chick or embryo. Antisense RNA transcribed from such vectors can hybridize to L1 ORF transcripts produced when the cells are infected by MDV, and thus are available to inhibit latency, and/or development of the infected cells into tumors.

Another variation of this embodiment involves the development of transgenic chickens which express antisense RNA to L1 ORF transcripts, wherein the transcription into antisense is under the control of an inducible promoter or a constitutive promoter. Methods known in the art for producing a transgenic chicken include the introduction of the genetic material into the chicken germ line cells by microinjection, viral infection, or embryonic stem cell transfer. Introduction of the genetic material, such as a sequence which can be transcribed into antisense to L1, results in lineages that carry the integrated genetic material. Detection of transgenics can be accomplished by isolating tissue cells and examining the isolated cells for integration of the transgene by Southern blot analysis, or for expression of the the antisense RNA to the L1 ORF by Northern blot analysis.

EXAMPLE 4

Methods for using L1 ORF-specific sequences in molecular diagnostic assays for the detection of MDV serotype 1

Figure 3:
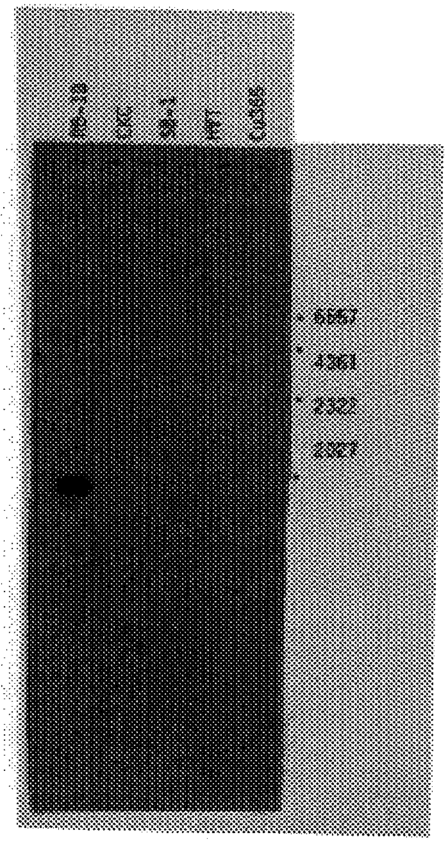
FIG. 3 represents Southern blot analysis for L1ORF sequences. DNA isolated from either RB1B-infected CKC (lane 1), uninfected chicken kidney cells (CKC) (lane 2), strain SB1 (lane 3), HVT (lane 4), or Cu365 (lane 5) was hybridized with a probe prepared from the L1 cDNA clone.

This embodiment is directed to nucleic acid molecules contained within the L1 ORF as molecular probes and/or primers in the detection of MDV serotype 1-specific genetic material. As disclosed herein, the L1 ORF maps to the BamH1-L, and -$Q_2$ regions of the MDV genome. Total DNA from CKC infected with serotype 1 MDV, CKC infected with serotype 2 MDV, and CKC infected with serotype 3 were analyzed for the presence of the L1 ORF. Total DNA preparations were made from CU115, a RB-1B (serotype 1)-transformed lymphoblastoid cell line; from uninfected CKC, from SB-1 (serotype 2 isolate)-infected CKC, and from HVT (serotype 3)-infected CKC. These DNA preparations were then digested with restriction enzyme BamHI, and the restriction digests were electrophoresed on an agarose gel. In the Southern blot analysis, the L1 probe (SEQ ID NO:2) was hybridized with the respective DNA preparations under low stringent conditions (allowing hybridization to sequences up to approximately 30% mismatches with the probe sequence). The results in FIG. 3 show that CU115 containing RB-1B MDV serotype 1 sequences (lane 1) contains L1 sequences as represented by hybridization with the L1 probe. However, L1 probe hybridization was not detected in uninfected CKC (negative control; lane 2), or SB-1-infected CKC (lane 3), or HVT-infected CKC (lane 4). Thus, L1 ORF-specific sequences do not appear to be present in MDV serotype 2 or HVT (serotype 3).

Therefore, in one embodiment of the present invention, nucleic acid sequences derived from the L1 ORF (SEQ ID NO:1) can be used in molecular diagnostic assays for detecting MDV serotype 1 genetic material. In one mode of this embodiment, nucleic acid molecules greater than 20 nucleotides in length may be generated by restriction enzyme digest of MDV genomic DNA and purified to isolate those molecules that are L1 ORF-specific, or synthesized using methods known in the art. Illustrative examples of such nucleic acid molecules include, but are not limited to, the L1 ORF (nucleotide positions 725–1045 of SEQ ID NO:1), and the L1 cDNA clone (SEQ ID NO:2). In another mode of this embodiment L1 ORF-specific oligonucleotides of desirably between approximately 15–30 nucleotides (but can be longer) can be synthesized for use as primers and/or probes in amplifying, and detecting amplified, nucleic acid molecules from MDV serotype 1 isolates or MDV serotype 1-infected cells. Illustrative examples of such nucleic acid molecules include, but are not limited to, SEQ ID NO:2, and SEQ ID NOs:3 to 13.

Recent advances in molecular biology have provided several means for enzymatically amplifying nucleic acid sequences. Currently the most commonly used method, PCR™ (polymerase chain reaction, Cetus Corporation) involves the use of thermostable DNA polymerase, known sequences as primers, and heating cycles which separate the replicating deoxyribonucleic acid (DNA) strands and exponentially amplify a gene of interest. Other amplification methods currently under development include LCR™ (ligase chain reaction, BioTechnica International) which utilizes DNA ligase, and a probe consisting of two halves of a DNA segment that is complementary to the sequence of the DNA to be amplified; enzyme QB replicase (Gene-Trak Systems) and a ribonucleic acid (RNA) sequence template attached to a probe complementary to the DNA to be copied which is used to make a DNA template for exponential production of complementary RNA; and NASBA™ (nucleic acid sequence-based amplification, Cangene Corporation) which can be performed on RNA or DNA as the nucleic acid sequence to be amplified.

Nucleic acid probes that are capable of hybridization with specific gene sequences have been used successfully to detect specific pathogens in biological specimens at levels of sensitivity suitable for molecular diagnostic assays. Coupled with a method that allows for amplification of specific target DNA sequences, species-specific nucleic acid probes can greatly increase the level of sensitivity in detecting organisms, or organism-specific genetic material in a clinical specimen. Use of these probes may allow direct detection without relying on prior cell culture techniques. One mode of this embodiment is directed to primers which amplify L1 ORF-specific sequences and to probes which specifically hybridize with these amplified DNA fragments. By using the nucleic acid sequences of the present invention and according to the methods of the present invention, specific sequences may be detected in the presence of 10 μg/ml extraneous DNA.

This embodiment is directed to L1 ORF-specific oligonucleotides which can be used to amplify L1 ORF-specific sequences, if present, from DNA extracted from clinical specimens containing serotype 1 genetic material; and to subsequently determine if amplification has occurred. In one embodiment of the present invention, a pair of L1 ORF-specific DNA oligonucleotide primers are used to hybridize to MDV genomic DNA that may be present in DNA extracted from a clinical specimen, and to amplify the specific segment of MDV genetic material between the two flanking primers using enzymatic synthesis and temperature cycling. Each pair of primers are designed to hybridize only to L1 ORF nucleotide sequences (a sequence contained within from nucleotide positions 725–1045 in SEQ ID NO:1) of the present invention to which they have been synthesized to complement; one to each strand of the double-stranded DNA. Thus, the reaction is specific even in the presence of microgram quantities of heterologous DNA. For the purposes of this description, the primer derived from the sequence of the positive (ORF) strand of DNA will be referred to as the "positive primer", and the primer derived from the sequence of the negative (complementary) strand will be referred to as the "negative primer".

Amplification of DNA may be accomplished by any one of the methods commercially available. For example, the polymerase chain reaction may be used to amplify the DNA. Once the primers have hybridized to opposite strands of the target DNA, the temperature is raised to permit replication of the specific segment of DNA across the region between the two primers by a thermostable DNA polymerase. Then the reaction is thermocycled so that at each cycle the amount of DNA representing the sequences between the two primers is doubled, and specific amplification of the L1 ORF DNA sequences, if present, results. Further identification of the amplified DNA fragment, as being derived from L1 ORF-specific sequences, may be accomplished by liquid hybridization. This test utilizes one or more labeled oligonucleotides as probes to specifically hybridize to the amplified segment of the L1 ORF. Detection of the presence of amplified L1 ORF-specific sequences may be accomplished using any one of several methods known in the art such as a gel retardation assay with autoradiography. Thus, the nucleic acid molecules of the present invention provide a basis for the synthesis of oligonucleotides which have commercial applications in diagnostic kits for the detection of MDV serotype 1. In a related embodiment, the oligonucleotides used as primers may be labeled directly, or synthesized to incorporate label. Depending on the label used, the amplification products can then be detected, after binding onto an affinity matrix, using isotopic or colorimetric detection.

DNA may be extracted from a clinical specimens which may contain MDV serotype 1 genetic material using methods known in the art. For example, cells contained in the specimen may be washed in TE buffer and pelleted by centrifugation. The cells then may be resuspended in 100 μl of amplification reaction buffer containing detergents and proteinase K. Using the polymerase chain reaction, the resultant sample may be composed of the cells in 10 mM Tris pH 8.3, 50 mM KCl, 1.5 mM $MgCl_2$, 0.01% gelatin, 0.45% NP40™, 0.045% Tween 20™, and 60 μg/ml proteinase K. The sample is incubated at 55° C. water bath for 1 hour. Following the incubation, the sample is incubated at 95° C. for 10 minutes to heat-inactivate the proteinase K. The sample may then be amplified in accordance with a protocol for enzymatic DNA amplification.

The L1 ORF-specific sequences may be amplified using any one of several protocols for amplifying nucleic acids by the polymerase chain reaction (See for example, Innis et al., 1990, *PCR Protocols: A Guide to Methods and Applications*, Academic Press, publs.). Oligonucleotides useful as primers or probes which specifically hybridize to the L1 ORF and used in DNA amplification and/or detection can be biochemically synthesized, using methods known in the art, from the nucleotide sequences disclosed in the present invention. The specificity of the oligonucleotides for the L1 ORF can be checked by a gene-bank database (Genbank) search for each individual sequence. In general, the oligonucleotides should be selected for low G-C content. Primers that has been used to amplify L1 ORF-specific sequences include SEQ ID NOs:10 and 11.

For detection purposes, oligonucleotides of the present invention may be end-labeled with a radioisotope. Probe sequences, internal to the two primers used for amplification of the gene sequence, may be end-labeled using $T_4$ polynucleotide kinase and gamma $^{32}P$ ATP. Twenty pMols of probe DNA in kinase buffer (50 mM Tris, pH 7.6, 10 mM $MgCl_2$, 5 mM dithiothreitol, 0.1 mM spermidine-HCl, 0.1 mM EDTA, pH 8.0) is mixed with 120 μCi of gamma $^{32}P$ ATP and incubated at 37° C. for 1 hour. Labeled probe is separated from unincorporated label on an 8% acrylamide gel run for 1 hour at 200 volts in Tris Borate EDTA (TBE) buffer at room temperature. Labeled probe is first located by exposing the acrylamide gel to x-ray film for three minutes. The resulting autoradiogram is then positioned under the gel, and the band containing the labeled probe was excised from the gel. The gel slice is pulverized in one milliliter of sterile distilled water, and the probe is eluted by shaker incubation overnight at 37° C. The eluted probe is separated from the gel fragments by centrifugation using a chromatography prep column. Radioactivity of the probe is determined, by counting one microliter of the labeled probe on a glass fiber filter, by liquid scintillation. Such a probe sequences may be chosen from the L1 ORF-specific sequence internal to the two primers used for amplification of L1 ORF-specific sequence.

Alternative methods known in the art may be used to improve the detection of amplified target sequences in accordance with the compositions and methods of the present invention. The sensitivity of detection of the amplified L1 ORF sequences can be improved by subjecting the sequences to liquid hybridization. Alternative methods of detection known in the art, in addition to gel electrophoresis and gel electrophoresis with Southern hybridization and autoradiography, that may be used with the compositions and methods of the present invention include: restriction enzyme digestion with gel electrophoresis; slot-blot hybridization with a labeled oligonucleotide probe; amplification with a radiolabeled primer with gel electrophoresis, Southern hybridization and autoradiography; amplification with a radiolabeled primer with dot blot and autoradiography; amplification with oligonucleotides containing affinity tags (ex. biotin, or one primer incorporating biotin and the other primer with a sequence specific for a DNA binding protein) followed by detection in an affinity-based assay (ex. ELISA); and amplification with oligonucleotides containing fluorophores followed by fluorescence detection, or other nonisotopic detectable labels.

EXAMPLE 5

This embodiment is directed to the use of the L1 ORF, or surrounding sequences controlling its expression, as an site in the MDV genome into which can be inserted a gene for expression, wherein the insertion interrupts L1 production but does not negatively affect the growth or replication of the viral vector. The resultant recombinant virus can be used as to deliver and express one or more immunogens in a vaccine formulation, or to express one or more biologically active polypeptides beneficial to the health/growth of poultry into which is introduced such recombinant vector.

Viral latency and transformation are known to be intimately related in MDV. It has been reported that a 0.6-kb BamHI-L-specific transcript (one of only two MDV-specific transcripts detected from CU210), is expressed in a relatively high amount in CU210, an REV-transformed cell line latently infected with MDV (Pratt et al., 1992, supra). The data presented in Example 1 clearly show that CU210 expresses the origin of the L1 and L1 cDNA clone, and the size of the L1 transcript is 0.6-kb. Thus, the L1 transcript appears to be associated with MDV latency in tumor cells. Further support for this association are the findings, presented in Examples 1 and 2, that a) L1 transcripts are more abundant (high level of transcription) in the MDV-transformed cell line CU41 than in lytically infected cells (low level of transcription); b) a high level of L1 transcripts are also detected in cells latently-infected with MDV, as evidenced by analysis of CU210; and as illustrated by the following experiment where L1 transcripts have been detected by Northern blot analysis of RNA from chicken spleen cells latently-infected with MDV. This embodiment of the present invention provides for the development of a Marek's disease virus which lacks oncogenicity. but does not negatively affect the growth or replication of the viral vector. As noted in U.S. Pat. No. 4,160,024 to Schat et al., unattenuated pathogenic strains of MDV have been unacceptable as vaccines for poultry because of their oncogenic potential. In one mode of this embodiment, the genomic region containing the L1 ORF of an unattenuated pathogenic strain of MDV can be genetically engineered not to express the 107 amino acid protein by inserting an exogenous or endogenous sequence into the L1 ORF to interrupt its expression (including by replacement).

Figure 7:
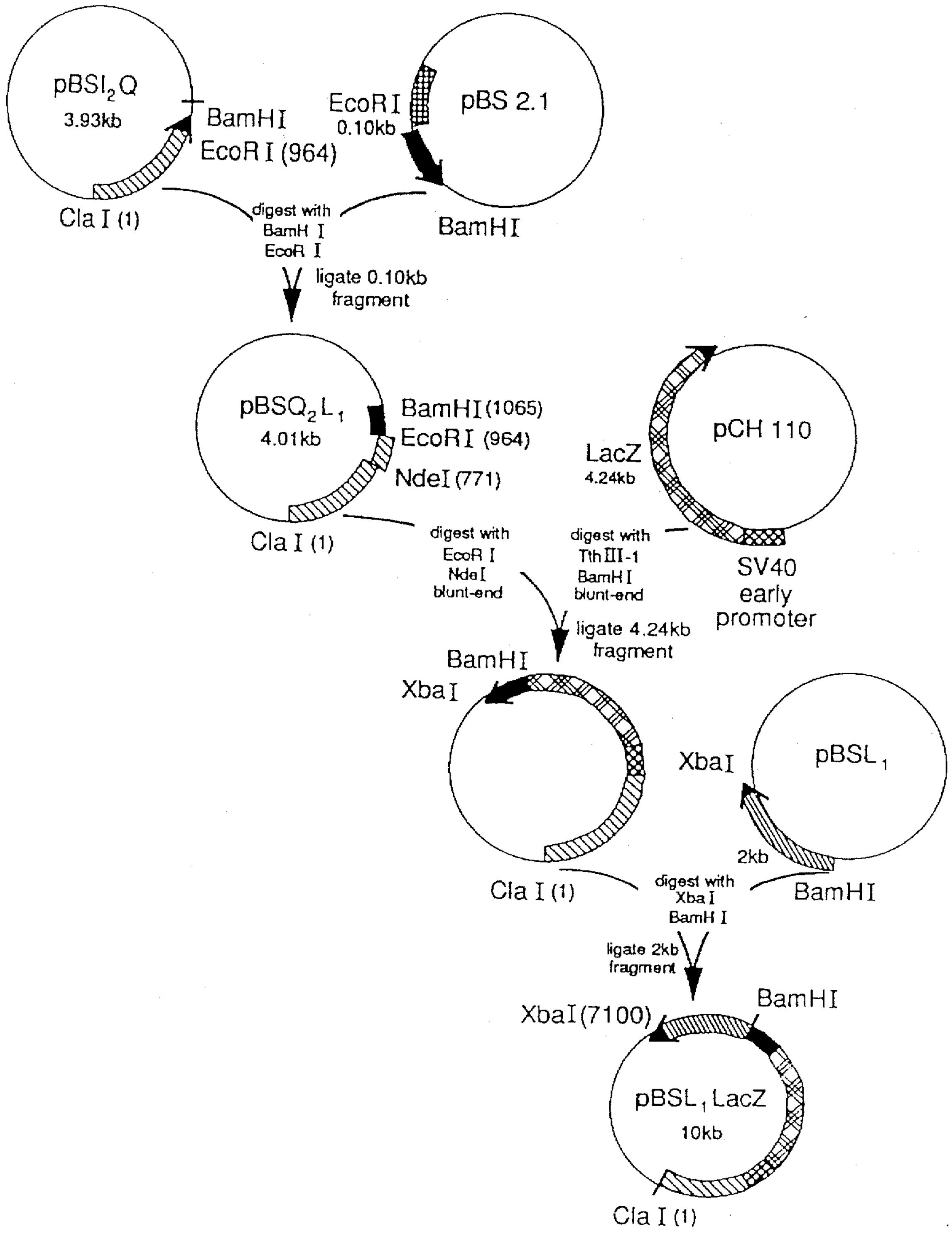
FIG. 7 is a schematic representation of the construction of an MDV vector, wherein the L1 open reading frame (L1ORF) is an insertion site for one or more genes to be expressed.

To illustrate this embodiment, a lacZ ORF under the control of its own promoter was inserted into a L1 ORF-containing plasmid as follows (see also FIG. 7). Plasmid pBSI2Q, containing the ClaI-EcoR1 fragment of the L1 ORF (nucleotide positions 1–965 of SEQ ID NO: 1) and a region of 730 bp upstream from the start codon was digested with EcoR1 and BamHI, and gel purified. pBS2.1, containing the 101 bp fragment of the Q2 region of the BamHI library of MDV DNA, as well as the remainder of the L1 ORF (nucleotide positions 966–1045 of SEQ ID NO:1), was restricted with EcoR1 and BamHI. The gel-purified 101 bp EcoR1-BamHI fragment was ligated to the EcoR1- BamHI digested pBSI2Q in forming pBSQ2LI. pBSQ2LI was digested with EcoR1 and NdeI to remove most of the L1 ORF, and the remainder of the plasmid was blunt-ended. A lacZ cassette containing the SV40 promoter, obtained from pCH110 and subsequently blunt-ended, was blunt-end ligated to the EcoR1-NdeI fragment of pBSQ2LI. The orientation of the lacZ cassette in the resulting plasmid was verified by restriction enzyme analysis, and two independent clones were analyzed for transient expression of LacZ in chicken embryo fibroblasts. This latter construct lacked an upstream MDV flanking sequence; therefore, a 2.1 kb BamH1-XbaI fragment from pBS.L was inserted directly behind the MDV-derived BamHI site. This 2.1 kb fragment contains a 1 kb Bg1II subfragment and a 0.8 BamHI-XhoI subfragment located directly upstream from the BamHI-Q2 fragment. The final resulting plasmid, pBSL1LacZ contained the lacZ, under the control of the SV40 early promoter, in forward orientation inserted in the remaining sequence of the L1 ORF.

Recombinant MDV was prepared as follows. Total MDV DNA was purified from the CV1988 strain (serotype 1) of MDV. MDV fragments containing lacZ were prepared by digesting pBSL1LacZ with ApaI and XbaI. Total MDV DNA (4 μg), and the ApaI and XbaI of pBSL1LacZ (different dilutions), were used to co-transfect chicken embryo fibroblasts (CEF) using the calcium precipitation method. Cultures were stained with 0.2 mg/ml a colorimetric substrate for β-galactosidase activity at 5 days post transfection; and blue-staining plaques were removed from the monolayer, trypsinized, and co-cultured with secondary CEF. Recombinant viruses were plaque-purified by repeating selection of lacZ-expressing plaques (usually 4–6 times) until stable recombinants were isolated. Recombinant viruses were tested and confirmed for the absence of the L1 ORF by using the polymerase chain reaction and two primers (SEQ ID NOs:12 and 13). Chicken embryo fibroblasts have been lyrically-infected with the plaque-purified lacZ-expressing recombinant MDV, thus demonstrating that the L1 ORF is non-essential for virus replication. Thus, in vitro studies show that by inserting an exogenous sequence into the L1 ORF, thereby interrupting transcription from the L1 ORF, a recombinant MDV that is unattenuated, pathogenic, and non-oncogenic may be developed which would be useful as a multivalent vaccine against MDV and other poultry pathogens.

In vivo experiments were performed to show that a recombinant MDV viral vector having an insertion in the L1 ORF can actually infect and replicate in chickens inoculated with the recombinant MDV viral vector. N-2a chickens were infected at 3 weeks of age with various MDV strains: UC (control); CVI988 (a serotype I attenuated MDV); 988L1LacZ A, 988L1LacZ B, (various independent clones in which a part of L1 ORF was replaced by lacZ as described above, and under the control of the SV40 early promoter), and 988US10LacZ (Sakaguchi et al., 1994, 12:953–955). At various days post infection (DPI), birds were analyzed by various assays including (a) isolating virus from the infected birds; (b) harvesting spleen cells and performing fluorescent antibody tests fox MDV; (c) smears of splenic lymphocytes and performing fluorescent antibody (FA) tests for MDV; (d) smears of splenic lymphocytes and testing for cells infected with MDV having β-galactosidase activity; and (e) presence and titer of anti-MDV antisera. Tables 3 and 4 illustrate pathogenesis of the various MDV strains at 5 days post infection. "Total positive" represents the number of birds positive for one or more of the assays/number of birds tested. Note that the recombinant MDV having an insertion in the L1 OF are pathogenic as they show infectivity and replication at 5 DPI.

TABLE 3

| Virus strain | *Virus isolation | *FA Spleens | *FA Smears | LacZ Smears* | Total positive |
|---|---|---|---|---|---|
| UC | 0/6 | 0/6 | 0/6 | NT | 0/6 |
| CV1988 | 16/17 | 15/17 | 16/17 | NT | 17/17 |
| 988L1LacZ A | 13/17 | 10/17 | 13/17 | 13/17 | 16/17 |
| 988L1LacZ B | 14/17 | 16/17 | 13/17 | 17/17 | 17/17 |
| 988US10LacZ | 10/17 | 13/17 | 7/17 | 13/17 | 14/17 |

*number of birds positive/total number of birds tested.
NT — not tested

TABLE 4

| Virus strain | Virus isolation % Positive | FA positive % Positive | LacZ positive % Positive |
|---|---|---|---|
| CVI988 | 94 | 94 | Not tested |
| 988L1LacZ A | 67 | 59 | 76 |
| 988L1LacZ B | 82 | 76 | 94 |
| 988us10LacZ | 59 | 47 | 59 |

A recombinant MDV prepared in accordance with the method of the present invention has been shown not only to grow and continuously infect chickens inoculated with the recombinant MDV, but also is immunogenic; i.e., induces anti-MDV antibody as shown in Table 5 for chickens at 20–21 DPI. Note that while low levels of induced antibody are detected, immunity to MDV is primarily cell-mediated immunity.

TABLE 5

| Virus | Virus | LacZ | anti-MDV Ab | | Total |
|---|---|---|---|---|---|
| strain | isolation | positive | # (+) | titer | positive |
| UC | 0/6 | 0/6 | 0/6 | 0 | 0/6 |
| CVI988 | 14/18 | 0/18 | 15/18 | 52 | 17/18 |
| 988L1LacZ A | 6/18 | 1/18 | 3/18 | 3 | 9/18 |
| 988L1LacZ B | 7/18 | 4/18 | 1/18 | 10 | 13/18 |
| 988US10LacZ | 3/17 | 3/17 | 5/17 | 10 | 9/17 |

The illustrative recombinant MDV contains the LacZ ORF into which a gene endogenous or exogenous to MDV may be inserted using any one of a multitude of available restrictions sites. Such restriction sites include Age I, Bau38 I, Aat II, EcoR V, BsaB I, Bcl I, BssH II, Eco47 III, Bst1107 I, Bs1W I, Nde I, EcoR I. Insertion of such gene using one or more restriction sites within the LacZ-ORF, and/or replacing the LacZ ORF with such gene using more than one restriction site, provides a convenient method for screening for recombinant virus with such insertion, as they should fail to express LacZ (nacZ(-)) which can be detected by screening the plaques for β-galactosidase activity using a substrate such as 5-bromo-4-chloro-3-indolyl-β-D-galactopyranoside. Various restriction sites in either the surrounding sequences of the L1 ORF which may contain regulatory sequences for expression from the L1 ORF; or within the L1 ORF, can be used to interrupt expression of (including removing all or a portion of) the L1 ORF in the process of making an MDV recombinant according to the present invention. For purpose of illustration, but not limitation, exemplary restriction sites include MscI, SspI, SalI, EcoRI, BamHI, BglII, HpaII, and HinfI.

For purposes of illustration and not limitation, the preceding example disclosed use of the LacZ ORF, operably linked to the SV40 early promoter, for insertion into the L1 ORF. Other control elements (promoters, regulatory sequences, etc.) that can be used in producing a recombinant MDV, are known to those skilled in the art. Viral promoters, such as those found in viral pathogens of poultry (listed below), may be particularly suited for such recombinant MDV. Successful expression of an endogenous or exogenous gene inserted into the L1 region of MDV, according to the present invention, requires that either the insert comprising such gene, or the remaining L1 ORF-specific sequences, or the vector itself, contain the necessary elements for transcription and translation which is compatible with, and recognized by poultry infected with the recombinant MDV. Using methods known in the art of molecular biology, including methods described above, various promoters and enhancers (control elements) can be incorporated into the vector or the remaining L1 ORF-specific sequences to increase the expression of the gene inserted into the L1 ORF, provided that such increased expression is compatible with the viability of the infected cells.

The selection of the promoter will depend on the expression system used. Promoters vary in strength, i.e. ability to facilitate transcription. Generally, for the purpose of expressing a cloned gene, it is desirable to use a strong promoter in order to obtain a high level of transcription of the gene and expression into gene product. Other control elements for efficient gene transcription or message translation include enhancers, and regulatory signals. Enhancer sequences are DNA elements that appear to increase transcriptional efficiency in a manner relatively independent of their position and orientation with respect to a nearby gene. Thus, depending on the expression vector system used, an enhancer may be placed either upstream or downstream from the gene inserted into the L1 ORF to increase transcriptional efficiency. Other control elements, such as transcription or translation initiation signals, can be used to regulate the expression of the gene inserted into the L1 ORF. Such control elements may be inserted into sequences of the recombinant MDV which are adjacent to the gene inserted into the L1 ORF-specific sequences, such as nearby vector DNA sequences, using recombinant DNA methods described herein for insertion of DNA sequences. Accordingly, an endogenous or exogenous gene can be ligated into the L1 ORF, in producing a recombinant MDV viral vector, and at a specific site in relation to the vector's control elements (promoter/regulatory elements) so that when the recombinant vector is used to infect the host, the gene inserted into the L1 ORF can be expressed in the host's cells.

In another mode of this embodiment, the recombinant MDV can be used as a vector in a multivalent vaccine by inserting one or more exogenous genes, under the control of its own promoter, an MDV promoter, other viral promoter, or a eukaryotic promoter(s) operably linked to the gene(s) inserted into the L1 ORF. Note that for this and related embodiments, the L1 ORF is present in the long inverted repeat region (IRL, FIG. 1), and therefore is also present in the long terminal repeat region (TRL, FIG. 1). Thus, since the L1 ORF is in a repeat region which is duplicated in the viral genome, insertion into the L1 ORF for gene expression may result in twice the amount of gene expression, as compared to if only a single insertion site were used. As demonstrated above, an exogenous gene can be inserted into the L1 ORF contained within a plasmid, and through homologous recombination with MDV serotype 1, a resultant recombinant virus is produced which is infective, replicative, and can express the inserted gene.

Desirably, one or more exogenous gene(s) inserted into the L1 ORF would encode protein which acts as an effective immunogen in inducing a protective immune response against its corresponding organism(s) of origin. Thus, the recombinant MDV could serve as a combined vaccine against Marek's disease and against other diseases of poultry. Examples of such antigens useful in a combined vaccine, and their corresponding pathogen and disease caused, are known in the art of veterinary medicine. Fox example, genes encoding antigens of infectious laryngotracheitis virus causing infectious laryngotracheitis, can be inserted into the L1 ORF for expression. In another example, one or more copies of the gene encoding the VP2 of infectious bursal disease virus, the birnavirus causing infectious bursal disease, can be inserted into the L1 ORF for expression. In another example, one or more copies of the gene encoding the viral hemagglutinin glycoprotein of the chicken fowlpox virus causing fowlpox, can be inserted into the L1 ORF for expression. In another example, one or more copies of the gene encoding the peplomer antigen of the infectious bronchitis virus, a coronavirus causing respiratory disease, can be inserted into the L1 ORF for expression. In yet another example, one or more copies of either or both of the gene encoding the HN antigen or the gene encoding the F antigen of Newcastle disease virus causing Newcastle disease, can be inserted in the L1 ORF for expression. Recombinant expression of Newcastle disease viral antigens in HVT has been described previously (Morgan et al. in *Proceedings XIX World's Poultry Congress*, Amsterdam, The Netherlands, 1992).

In another mode of this embodiment, one or more copies of an endogenous (MDV) gene, whose gene product is an antigen capable of eliciting a protective immune response, can be inserted within the L1 ORF to increase antigen expression for vaccine purposes. For example, glycoprotein B (gB) is a major glycoprotein produced by MDV, which when inoculated into chickens results in the production of neutralizing antibody (Nazerian et al., 1992, *J. Virol.* 66:1409–1413). Multiple copies of the gene encoding gB can be inserted in the L1 ORF under the control of a MDV promoter to make a more effective recombinant vaccine against Marek's disease. One or more copies of genes encoding other major viral glycoproteins of MDV, such as gA, may be inserted along with gB into the recombinant MDV to induce a protective immune response consisting of either cellular immunity, or humoral immunity.

It should be understood that while the invention has been described in detail herein, the examples were for illustrative purposes only. Other modifications of the embodiments of the present invention that are obvious to those skilled in the art of molecular biology, veterinary medicine, and related disciplines are intended to be within the scope of the appended claims.

We claim:

1. An isolated and purified nucleic acid molecule encoding a Marek's disease virus polypeptide, wherein the polypeptide consists of the amino acid sequence as shown in SEQ ID NO: 1.

2. An isolated and purified nucleic acid molecule which is a nucleotide sequence selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and an open reading frame located between nucleotide positions 725–1045 of SEQ ID NO:1.

3. A recombinant vector containing the nucleic acid molecule according to claim 1, wherein the nucleic acid molecule is operably linked to one or more control elements for expression.

4. A recombinant vector containing the nucleic acid molecule according to claim 2, wherein the nucleic acid molecule is the open reading frame which is operably linked to one or more control elements for expression.

5. A recombinant serotype 1 Marek's disease virus strain, wherein said strain is genetically engineered by inserting one or more endogenous or exogenous genes into a nucleotide sequence consisting of SEQ ID NO:1 to interrupt expression of L1 ORF located between nucleotide positions 725–1045 of SEQ ID NO:1; wherein said one or more genes is operably linked to one or more control elements for expression.

6. The recombinant Marek's disease virus according to claim 5, wherein said one or more genes is inserted into the L1 ORF.

7. The recombinant Marek's disease virus according to claim 5, wherein said one or more genes is an endogenous gene encoding an antigen selected from the group consisting of gB, gA, and a combination thereof.

8. The recombinant Marek's disease virus according to claim 6, wherein said one or more genes is an endogenous gene encoding an antigen selected from the group consisting of gB, gA, and a combination thereof.

9. The recombinant Marek's disease virus according to claim 5, wherein said one or more genes is an exogenous gene encoding an antigen selected from the group consisting of the VP2 of infectious bursal disease virus, the viral hemagglutinin glycoprotein of the chicken fowlpox virus, the peplomer antigen of the infectious bronchitis virus, the HN antigen of Newcastle disease virus, the F antigen of Newcastle disease virus, and a combination thereof.

10. The recombinant Marek's disease virus according to claim 6, wherein said one or more genes is an exogenous gene encoding an antigen selected from the group consisting of the VP2 of infectious bursal disease virus, the viral hemagglutinin glycoprotein of the chicken fowlpox virus, the peplomer antigen of the infectious bronchitis virus, the HN antigen of Newcastle disease virus, the F antigen of Newcastle disease virus, and a combination thereof.

11. A multivalent vaccine comprising the recombinant Marek's disease virus according to claim 5.

12. A multivalent vaccine comprising the recombinant Marek's disease virus according to claim 6.

13. A multivalent vaccine comprising the recombinant Marek's disease virus according to claim 7.

14. A multivalent vaccine comprising the recombinant Marek's disease virus according to claim 8.

15. A multivalent vaccine comprising the recombinant Marek's disease virus according to claim 9.

16. A multivalent vaccine comprising the recombinant Marek's disease virus according to claim 10.

17. A process of preparing a recombinant Marek's disease virus comprising inserting one or more endogenous or exogenous genes, operably linked to a control element for expression, into a region of a serotype 1 Marek's disease virus genome, wherein said region consists of the nucleotide sequence of SEQ ID NO:1, and wherein said one or more genes and the control element are incorporated into a region of the Marek's disease virus genome, and wherein said incorporation interrupts expression from an L1 ORF present in the genome but allows expression of said one or more incorporated genes.

* * * * *